US00PP20337P3

(12) United States Plant Patent

Dozier, Jr. et al.

(10) Patent No.: US PP20,337 P3

(45) Date of Patent: Sep. 22, 2009

(54) CHESTNUT PLANT NAMED 'AU BUCK II'

(50) Latin Name: *Castanea mollissima*
Varietal Denomination: AU Buck II

(75) Inventors: W. Alfred Dozier, Jr., Opelika, AL (US); Joseph Daniel Norton, Auburn, AL (US); Curtis J. Hansen, Opelika, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 12/012,025

(22) Filed: Jan. 30, 2008

(65) Prior Publication Data

US 2009/0210972 P1 Aug. 20, 2009

(51) Int. Cl.
*A01H 5/00* (2006.01)

(52) U.S. Cl. ..... Plt./152

(58) Field of Classification Search ..... Plt./152
See application file for complete search history.

(56) References Cited

OTHER PUBLICATIONS

Lin ye ke ji et al., "Forest Science & Technology", Jan. 1989, pp. 16-18, Baker Auxiliary Stacks SD1. L56, No. 2-1990.

Crane, H.L. et al., Nut Breeding, U.S. Department of Agriculture Yearbook, Jan. 1937, pp. 827-837.

Hemming, E. Sam, "Chinese Chestnut in Maryland", Jan. 1944, pp. 32-34, A.R. Northern Nut Growers Assoc.

Kim, Kap Duk et al., Studies on the Farmers Cultivating Chestnut Orchards in Korea and its Financial Analysis, Jan. 1971, pp. 51-74, Bull. Seol. Nut. Univ.Fores., No. 8.

Snare, Lester, Chestnuts Production, Jan. 1996, pp. 422-427, NSW Agriculture, Agfact H3.1.50., hhtp://www.rirdc.gov.au/pub/handbook/chestnuts.pdf.

Harris, Hubert et al., Three Chinese Chestnuts: AU-Cropper, AU-Leadder, and AU-Homestead-Their History and Production, Mar. 1980, pp. 3-8, Agricultural Experiment Station Auburn University Circular 247.

*Primary Examiner*—Annette H Para
(74) *Attorney, Agent, or Firm*—Haverstock & Owens LLP

(57) ABSTRACT

'AU Buck II' is a new and distinct Chinese chestnut cultivar that is blight resistant, precocious and prolific. It produces a large nut. Nut drop begins about September 15 and continues for a 6–7 week period. A large percentage of the nuts drop during the first three weeks after the beginning of nut drop. 'AU Buck II' nuts mature and start dropping during the early phase of the normal ripening period that most Chinese chestnut cultivars mature and drop nuts in the area. 'AU Buck II' is a large tree that was 9.14 meters tall, with a canopy area of 101.36 square meters at 15-years of age. 'AU Buck II' is the second cultivar to mature and drop nuts in a series of four Chinese chestnut cultivars that will provide for a continuous nut drop of a high energy wildlife food source from late August through mid-to-late November.

3 Drawing Sheets

Latin name of the genus and species of the plant claimed: *Castanea mollissima* Blume.

Variety denomination: 'Au Buck II'.

BACKGROUND OF THE INVENTION

A Chinese chestnut planting was established at Auburn University, Auburn, AL, from nuts collected in China. The planting was established on the United States Department of Agriculture Horticulture Farm which in later years became the Mainstation Horticulture Farm. Precocious and prolific-bearing, blight resistant seedlings were selected for nut appearance, size and quality. Each generation of seedlings were the product of controlled mass pollination from the most promising seedlings selected from the previous generation. 'AU Cropper', 'AU Leader' and 'AU Homestead' were released from a second generation of approximately 2000 seedlings. A planting of third generation seedlings from controlled mass pollination of 'AU Leader', 'AU Homestead' and 'AU Cropper' was established at the Auburn University Piedmont Substation at Camp Hill, AL.

SUMMARY OF THE INVENTION

'AU Buck II' is an open pollinated seedling of 'AU Homestead'.

The present invention relates to a new and distinct Chinese chestnut cultivar that is blight resistant, precocious, produces large sized nuts (16.6 g), and begins nut drop about September 15 and continues for a 6–7 week period. A large percent of the nuts drop during the first three weeks after nut drop begins. The nuts mature and start dropping during the early part of the normal ripening period for most Chinese chestnut cultivars in this area. The large crop of large sized nuts is an excellent high energy food source for wildlife such as deer and squirrels. The original 15-year old 'AU Buck II' tree is a large tree, 9.14 meters tall, with a canopy width of 11.35 meters, and a canopy area of 101.36 square meters. The tree has a trunk diameter of 37.9 cm at breast height. The 'AU Buck II' produced nuts the third year after transplanting, has produced a large crop annually for the size of tree, and produced 127.9 kg (282 pounds) of nuts in 2006.

'AU Buck II' cultivar is the second cultivar to mature and drop nuts in a series of four Chinese chestnut cultivars that will provide a continuous nut drop of a high energy wildlife food source from late August through mid-to-late November. 'AU Buck I', 'AU Buck III' and 'AU Buck IV' are the other three cultivars, which are disclosed in U.S. patent application No. 12/012,091, filed on Jan. 30, 2008, and entitled "CHESTNUT PLANT NAMED 'AU BUCK I'", U.S. patent application No. 12/012,110, filed on Jan. 30, 2008, and entitled "CHESTNUT PLANT NAMED 'AU BUCK III'" and U.S.

patent application No. 12/012,112, filed on Jan. 30, 2008, and entitled "CHESTNUT PLANT NAMED 'AU BUCK IV'", which are hereby incorporated by reference.

The new cultivar is able to be asexually reproduced by budding or grafting onto a seedling Chinese chestnut rootstock. The unique characteristics come true to form and are established and transmitted through asexual propagation.

DETAILED BOTANICAL DESCRIPTION

Figure 1:
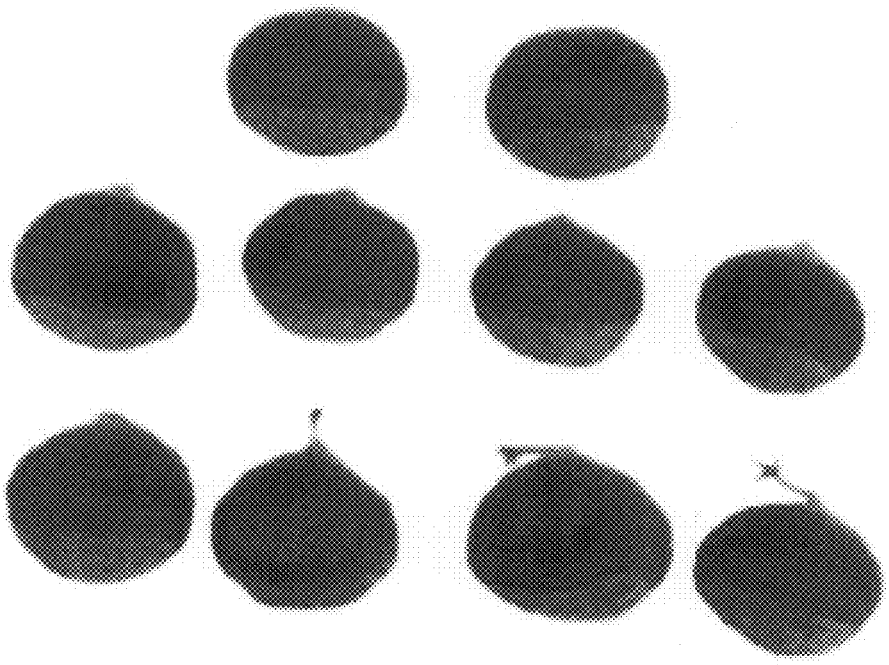
FIG. 1 is a photograph of nuts of the 'AU BUCK II' cultivar.
Figure 2:
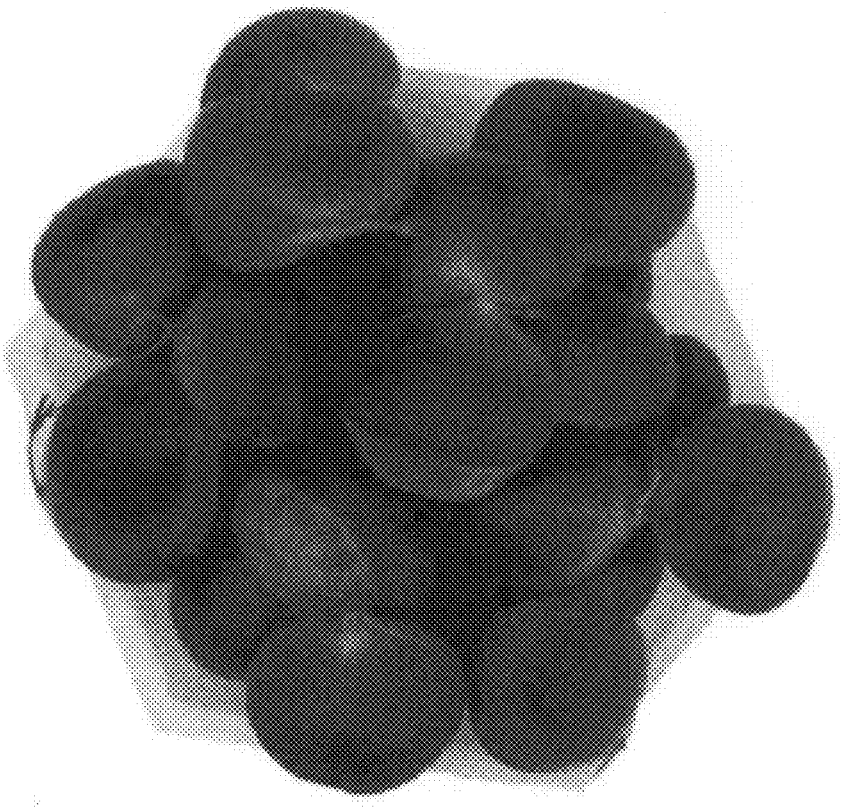
FIG. 2 is a photograph of nuts of the 'AU BUCK II' cultivar.
Figure 3:
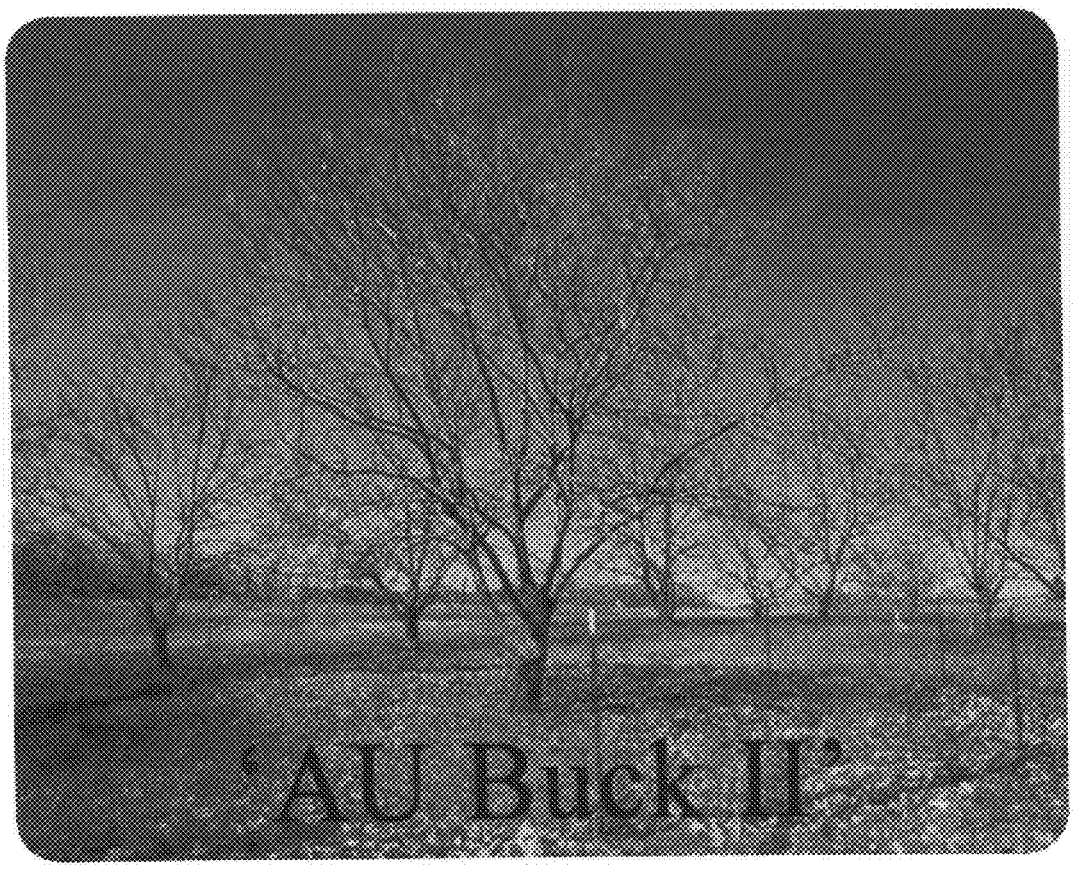
FIG. 3 is a photograph of a tree of the 'AU BUCK II' cultivar.

The Chinese chestnut, *Castanea mollissima* Blume, is a cold, hardy, temperate zone species native to China. It can be grown between 30° and 50° latitudes. The Chinese chestnut is resistant to chestnut blight fungus *Cryphonectria parasitica*. Generally, Chinese chestnuts are grown on a wide range of soils, but well-drained, deep and fertile soils are considered the best. Soils should be slightly acidic with pH 5.6–6.5. The name *mollissima* means soft hair and this species is recognized by dense hair on young leaves and downy yellow terminal parts of the shoots in winter. The leaf blade is thicker, and, in general, mature leaves are broader than those of other species. The nuts have a small scar or hilum. The pellicle or thin membranous skin on the nuts is thin and peels readily from the kernel. The trees are a spreading type and long-lived with a round top. The trees have bark with furrows and buds with 3–4 scales and leaves are 2 ranked, serrated with numerous parallel veins.

Chestnuts are monoecious and staminate flowers appear on erect cylindrical catkins with 10–20 stamens and 6-parted calyx. Pistillate flowers are borne on a lower part of the upper staminate catkins and rarely on separate catkins usually 3 in a prickly symmetrical involucre with 7–9 styles and a 6-celled ovary. Nuts are small, brown with a pale scar at the base. Generally, 1–3 nuts per involucre or bur are present.

'AU Buck II' is a tall tree that is obovate in shape with high, diffuse and upright branches. The original 15-year old tree is 9.14 meters (29.96 feet) tall with a trunk diameter at breast height of 37.90 cm (14.92 inches). The canopy is 11.35 meters (37.20 feet) wide and covers an area of 101.36 square meters (1091.0 square feet). The average nut length is 30.70 mm (1.21 inches) and the average nut width is 37.70 mm (1.48 inches). The nuts start dropping about September 15 and continue to drop for a 6 to 7 week period. A large percent of the nuts drop during the first three weeks after nut drop begins. The nuts mature and start dropping during the early part of the normal ripening for most Chinese chestnuts cultivars in this area. 'AU Buck II' is a precocious and prolific fruiting cultivar.

In the planting at the Piedmont Substation, Camp Hill, AL., accurate yields could not be obtained due to extremely heavy wildlife (deer and turkey) feeding. Therefore, the trees were rated for crop load each year. 'AU Buck II' has been a producer of a large crop load each season. In the fall of 2006, individual trees were caged with 6 foot (1.83 meters) tall chicken wire prior to nut drop to exclude wildlife and nuts were picked up daily during nut drop. The original 15-year old 'AU Buck II' tree produced 127.9 kg (282.0 pounds) of nuts in 2006. This is a much greater yield than the yields of similar aged trees.

The table below illustrates the specific differences between the 'AU BUCK II' cultivar and the 'REVIVAL' cultivar.

The botanical details of this new and distinctive variety of chestnut tree - with color definitions (except those in common color terms) referenced to Royal Horticultural Society's Colour Chart (RHS) and color was also determined using an electronic spectrophotometer to determine hue angle and Chroma (spectrophotometer model CM-2002; Minolta Camera Co., Japan).

10/23 'AU BUCK II' CHESTNUT

Tree:

Size (at maturity) - large-fifteen year old original tree is 9.14 meters tall with a canopy width of 11.35 meters and a canopy area of 101.36 sq. meters Tree shape is round.
Vigor - very vigorous Trunk:

Form - upright with branches low and diffuse
Texture - relatively smooth
Color of bark - brown RHS N200B, Chroma C* 11.85, hue angle 85.23

Branches:

Form - upright and spreading
Texture - relatively smooth
Lenticels - few, small
Branching habit - low and spreading
Color - new wood: brown, RHS 200C, Chroma C* 13.80, hue angle 71.55, mature wood: grey-brown RHS N199A Chroma C* 13.69, hue angle 91.59

Foliage:

Quantity - abundant
Density - dense

Leaves:

Size - large. Length (cm) 20.5 (17.5-23.5) [20]
width (cm) 8.2 (7.2-9.3) [20]
leaf ratio 2.5 (2.1-3.0) [20]
Shape - oblong-elliptic to obovate
leaf tip - acuminate to acute
leaf base - rounded; equal to oblique
Thickness - thick. Leaf venation 1° pinnate: 2° ± parallel, prominent abaxially
Texture - moderately coriaceous
Margin - weakly to coarsely serrate; teeth ascending
Petiole - length 0.9 cm (0.5-1.8) [20]
Petiole pubescence - sparingly to generously pubescence of simple hairs
Color - adaxial surface, glabrous blade; scattered simple hairs on main veins medium green; moderately shiny, RHS 147A, Chroma C* 14.62, hue angle 120.75
abaxial surface, moderately to densely stellate pubescence on blade; simple hairs along main veins, RHS 147B, Chroma C* 18.44, hue angle 110.70

Bloom:

Amount of bloom - heavy
Color - at anthesis, 161D greyed-yellow group, 157D green-white group, 155C white group
Blooming period - mid-May. After foliation in April.
Age at which tree starts flowering - early, 2-3 years alter graft replacement.
Male flower - Catkin length (cm)-13.7 (11.8-15.7) [15]
Male flower - stamen number per catkin-11.3 (10-12) [15]
Female flower - flower number per bur - 3
Female flower - style number per flower 6.7 (5-8) [12]

Crop:

Bearing - regular annual bearer
Productivity - prolific
Ripening period - long, nuts begins dropping September 14 and continues for a 4-5 week period.
Distribution of nuts on tree - well distributed, fruits on terminals with 2-4 burs per terminal.
Tenacity - burs crack while on tree and nuts release and drop from bur.

-continued

Hull:

Description - spiny round bur
Size - 2.98-3.71" in diameter
Number of nuts - 2-3 per bur
Dehiscence - splits easily when still on tree
Color - yellow-green at dehiscence, RHS N144C
Nut:

Size - very large; average size- 1.21" × 1.48" × 0.81".
Average weight - 16.6 grams 27 (23-33) nuts per pound.
Form - very large, broader than long, flattened on 1 side, occ. 2, mostly hemispheric on other side; rounded basally, almost flat distally with little or no tip.
Blossom end - small pointed tip
Basal end - flattened
Color - light brown, RHS 200B, Chroma C* 14.03, hue angle 40.05
Pubescence - mixed long and short, fine, white hairs densely covering the ⅛ to ¼ end, otherwise sparse and glabrate elsewhere
Shell - thin
Hardness of shell - relatively hard, yet not rigid
Texture of shell - smooth
Percentage of kernel to nut - very high-90-95%
Kernel:

Size - almost as large as nut size
Form - same as nut shape
Pellicle - thin
Flavor - excellent, very sweet
Color - straw color, RHS 152D, Chroma C* 45.86, hue angle 81.35
Resistance to insects: no unusual susceptibilities noted
Resistance to disease: no susceptibilities to disease noted
The chestnut tree and its nuts herein described may vary in slight detail due to climatic and soil conditions under which the variety may be grown; the present description being of the variety as grown in Camp Hill, Ala.

The botanical details of this variety of chestnut tree - with color definitions (except those in common color terms) referenced to Maerz and Paul Dictionary of Color-are as follows:

'REVIVAL'

Tree:

Size (at maturity) - large
Vigor - very vigorous
Trunk:

Form - upright with branches spreading in upper reaches of tree.
Texture - relatively smooth
Color of bark - Silvergray (13-A-1)
Branches:

Form - strong
Texture - relatively smooth
Lenticels - few, small
Branching habit - spreading in upper region of tree
Color - new wood: reddish brown and glossy, mature wood: silver gray
Foliage:

Quantity - abundant
Density - dense
Leaves:

Size - large. Average length - 5-7" (including petiole).
Average width - 2"
Shape - oblong with acute tip and rounded base
Thickness - thick
Texture - smooth
Margin - dentate
Petiole - length: medium. Thickness: medium.
Color - Top side - glossy dark green (22-L-12).
Under side - lighter green (21-D-7).

-continued

Bloom:

Amount of bloom - heavy
Color - cream white (17-B-1)
Blooming period - late. After leaf out in April
Age at which tree starts flowering - early; 2-3 years years after graft replacement.
Crop:

Bearing - regular (yearly) bearer
Productivity - prolific
Ripening period - short. September 15-October 1.
Distribution of nuts on tree - well distributed
Tenacity - burrs crack while on tree and nuts easily release, many falling by themselves
Hull:

Description - spiny, round burr
Size - 3-4" in diameter
Number of nuts - 2-3 per burr
Dehiscence - splits easily when still on tree. Some entire burrs split and fall to ground
Color - brown (15-A-8)
Nut:

Size - large. Average size - 1⅛" × 1⅛" × 1" thick.
Average weight - 24-32 nuts per pound
Form - broad and ovoid on one side, flat on other side
Blossom end - pointed tip
Basal end - flattened
Color - India Red (7-L-6).
Shell - thin
Hardness of shell - relatively hard, yet not rigid
Texture of shell - smooth
Percentage of kernel to nut - very high (95%)
Kernel:

Size - almost as large as nut size
Form - same as nut shape
Pellicle - thin
Flavor - excellent. Very sweet.
Color - Oyster white (10-B-1)
Resistance to insects: no unusual susceptibilities noted
Resistance to disease: very high inherent resistance to chestnut bark fungus (*Endothia parastica*), no other susceptibilities to any other disease
The chestnut tree and its nuts herein described may vary in slight detail due to climatic and soil conditions under which the variety may be grown; the present description being of the variety as grown in Alachua, Fla.

'Au Buck II' is different from 'AU Gobbler I' in several ways. For example, the size of the trees, the trunk forms and colors, the branches, the leaves, the crop and the nuts have differences. Specifically, the 'AU Buck II' tree is shorter with a canopy area larger than the 'AU Gobbler I' tree. The 'AU Buck II' branches are upright/spreading, low/spreading and brown (new) or grey-brown (mature); whereas, the 'AU Gobbler I' branches are upright, high, diffuse and brown (new) or greyed-green (mature). The leaves differ in size, shape, margin, petiole and color. The ripening period for the 'AU Buck II' is around September 14 and continues for a 4–5 week period, but the 'AU Gobbler I' ripening period is around August 25 and continues for 4–5 weeks. The average weight of the nuts of 'AU Buck II' is 16.6 grams versus 7.7 grams for 'AU Gobbler I'. Furthermore, 'AU Buck II' has roughly 27 nuts per pound, and 'AU Gobbler I' has roughly 59 nuts per pound.

'AU Buck II' is different from 'AU Gobbler II' in several ways. For example, the trees, the trunk colors, the branch colors, the leaves, the crop and the nuts have differences.

Specifically, the 'AU Buck II' tree is taller with a canopy width and canopy area larger than the 'AU Gobbler II' tree. The 'AU Buck II' branches are brown (new) or grey-brown (mature); whereas, the 'AU Gobbler II' branches re brown (new) or greyed-green (mature). The leaves differ in size, shape, margin and color. The ripening period for the 'AU Buck II' is around September 14 and continues for a 4–5 week period, but the 'AU Gobbler II' ripening period is around September 5 and continues for 4–5 weeks. The average weight of the nuts of 'AU Buck II' is 16.6 grams versus 5.7 grams for 'AU Gobbler II'. Furthermore, 'AU Buck II' has roughly 27 nuts per pound, and 'AU Gobbler II' has roughly 65–101 nuts per pound.

'AU Buck II' is different from 'AU Premier' in several ways. For example, the trees, the trunk colors, the branch colors, the leaves, the crop and the nuts have differences. Specifically, the 'AU Buck II' tree is taller with a canopy width and canopy area larger than the 'AU Premier' tree, The 'AU Buck II' has a grey-brown trunk, and the 'AU Premier' has a greyed-green trunk. The 'AU Buck II' branches are brown (new) or grey-brown (mature); whereas, the 'AU Premier' branches are brown (new) or greyed-green (mature). The leaves differ in size, shape, thickness, texture, margin, petiole and color. The ripening period for the 'AU Buck II' is around September 14, and the 'AU Premier' ripening period is early September through mid-November. The average weight of the nuts of 'AU Buck II' is 16.6 grams versus 1.26 grams for 'AU Premier'. Furthermore, 'AU Buck II' has roughly 27 nuts per pound, and 'AU Premier' has roughly 360.3 nuts per pound.

'AU Buck II' is different form 'AU Encore' in several ways. For example, the trees, the trunk colors, the branch colors, the leaves, the crop and the nuts have differences. Specifically, the 'AU Buck II' tree is taller with a canopy width and canopy area larger than the 'AU Encore' tree. The 'AU Buck II' has a grey-brown trunk, and the 'AU Encore' has a greyed-green trunk. The 'AU Buck II' branches are brown (new) or grey-brown (mature); whereas, the 'AU Encore' branches are brown (new) or greyed-green (mature). The leaves differ in size, shape, thickness, texture, margin, petiole and color. The ripening period for the 'AU Buck II' is around September 14, but the 'AU Encore' ripening period is late September through late November. The average weight of the nuts of 'AU Buck II' is 16.6 grams versus 2.4 grams for 'AU Encore'. Furthermore, 'AU Buck II' has roughly 27 nuts per pound, and 'AU Encore' has roughly 189.2 nuts per pound.

What is claimed is:

1. A new and distinct cultivar of the species *Castanea mollissima* Blume named 'AU BUCK II' as described and illustrated herein.

* * * * *

'AU Buck II'

'AU Buck II'

UNITED STATES PATENT AND TRADEMARK OFFICE

CERTIFICATE OF CORRECTION

PATENT NO. : PP 20,337 P3
APPLICATION NO. : 12/012025
DATED : September 22, 2009
INVENTOR(S) : Dozier, Jr. et al.

It is certified that error appears in the above-identified patent and that said Letters Patent is hereby corrected as shown below:

At column 4, line 53, please replace "alter" with "after" so that the sentence reads -- Age at which tree starts flowering - early, 2-3 years after graft. --

At column 5, line 28, please replace "Resistance to insects: no unusual susceptibilities noted" with "Resistance to insects: no unusual susceptibilities noted", so that the sentence reads -- Resistance to insects: no unusual susceptibilities noted --

At column 5, line 29, please replace "Resistance to disease: no susceptibilities to disease noted" with "Resistance to disease: no susceptibilities to disease noted", so that the sentence reads -- Resistance to disease: no susceptibilities to disease noted --

At column 6, line 37, please replace "Resistance to insects: no unusual susceptibilities noted" with "Resistance to insects: no unusual susceptibilities noted", so that the sentence reads -- Resistance to insects: no unusual susceptibilities noted --

At column 6, line 38, please replace "Resistance to disease: no susceptibilities to disease noted" with "Resistance to disease: no susceptibilities to disease noted", so that the sentence reads -- Resistance to disease: no susceptibilities to disease noted --

Signed and Sealed this

Third Day of November, 2009

David J. Kappos

David J. Kappos
*Director of the United States Patent and Trademark Office*